(12) United States Patent
Noel et al.

(10) Patent No.: US 8,597,267 B2
(45) Date of Patent: Dec. 3, 2013

(54) TAMPON HAVING AT LEAST ONE PHYSICAL DISCONTINUITY

(75) Inventors: John Richard Noel, Cincinnati, OH (US); Leslie Lynn Crosby, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 233 days.

(21) Appl. No.: 11/787,816

(22) Filed: Apr. 18, 2007

(65) Prior Publication Data

US 2008/0262463 A1    Oct. 23, 2008

(51) Int. Cl.
*A61F 13/15*   (2006.01)
*A61F 13/20*   (2006.01)
*A61F 13/22*   (2006.01)

(52) U.S. Cl.
USPC . 604/385.15; 604/358; 604/365; 604/385.01; 604/378; 604/379; 604/380; 604/382; 604/385.17

(58) Field of Classification Search
USPC ............... 604/11, 13, 14, 358, 367, 374, 378, 604/385.01, 385.02, 385.17, 385.18, 904; 28/118, 121; 424/430, 431
See application file for complete search history.

(56) References Cited

U.S. PATENT DOCUMENTS

| | | | |
|---|---|---|---|
| 2,430,250 A * | 11/1947 | Seidler | 604/11 |
| 2,529,183 A | 11/1950 | Parish | |
| 2,566,190 A | 8/1951 | Greiner et al. | |
| 2,706,986 A | 4/1955 | Carrier | |
| 2,858,831 A | 11/1958 | Graham, Jr. | |
| 2,905,175 A | 9/1959 | Schwartz | |
| 3,058,468 A | 10/1962 | Griswold et al. | |
| 3,359,981 A * | 12/1967 | Hochstrasser | 604/374 |
| 3,595,236 A * | 7/1971 | Corrigan et al. | 604/363 |
| 3,610,243 A | 10/1971 | Jones, Sr. | |
| 4,018,225 A * | 4/1977 | Elmi | 604/369 |
| 4,027,673 A * | 6/1977 | Poncy et al. | 604/369 |
| 4,077,409 A | 3/1978 | Murray et al. | |
| 4,175,561 A | 11/1979 | Hirschman | |
| 4,217,900 A | 8/1980 | Wiegner et al. | |
| 4,335,720 A | 6/1982 | Glassman | |
| 4,714,466 A * | 12/1987 | Dohzono et al. | 604/378 |

(Continued)

FOREIGN PATENT DOCUMENTS

FR    1 461 789 A    2/1967

OTHER PUBLICATIONS

PCT Search Report—PCT/IB2008/051447, Mailing date Jul. 21, 2008, pp. 1-6.

*Primary Examiner* — Adam Marcetich
(74) *Attorney, Agent, or Firm* — Sarah M. DeCristorfaro; Roddy M. Bullock; Megan C. Hymore

(57) ABSTRACT

A tampon having at least one physical discontinuity is provided. The physical discontinuity, or physical discontinuities, are located in the compressed absorbent member and may be made in the tampon pledget before the pledget is compressed into the absorbent member. The physical discontinuities partially isolate a portion, or portions, of the tampon from the rest of the tampon. The partial isolation of a portion of the tampon reduces the amount of menses absorbed by that portion, which could be transported to the rest of the tampon through wicking. The concentration of menses absorption in a portion allows that portion have a higher level of expansion than the rest of the tampon to prevent menses from leaking out of the vaginal opening.

11 Claims, 7 Drawing Sheets

(56) References Cited

U.S. PATENT DOCUMENTS

| | | | |
|---|---|---|---|
| 4,835,042 A * | 5/1989 | Dohzono et al. | 428/218 |
| 5,047,024 A * | 9/1991 | Glassman | 604/380 |
| 5,112,348 A | 5/1992 | Glassman | |
| 5,153,971 A * | 10/1992 | Van Iten | 28/118 |
| 5,185,010 A * | 2/1993 | Brown, Jr. | 604/379 |
| 5,350,371 A | 9/1994 | Van Iten | |
| 5,383,891 A | 1/1995 | Walker | |
| 5,387,206 A * | 2/1995 | Valentine et al. | 604/358 |
| 5,542,914 A | 8/1996 | Van Iten | |
| 5,609,586 A * | 3/1997 | Zadini et al. | 604/358 |
| 6,177,608 B1 * | 1/2001 | Weinstrauch | 604/380 |
| 6,186,995 B1 * | 2/2001 | Tharpe, Jr. | 604/385.18 |
| 6,206,867 B1 * | 3/2001 | Osborn et al. | 604/385.18 |
| 6,500,140 B1 * | 12/2002 | Cole et al. | 604/15 |
| 6,558,370 B2 * | 5/2003 | Moser | 604/317 |
| 6,740,070 B2 * | 5/2004 | Agyapong et al. | 604/385.18 |
| 6,758,839 B2 * | 7/2004 | Lochte et al. | 604/385.18 |
| 6,758,840 B2 * | 7/2004 | Knox | 604/385.18 |
| 6,768,040 B1 * | 7/2004 | Sessions et al. | 602/56 |
| 6,840,927 B2 * | 1/2005 | Hasse et al. | 604/385.18 |
| 6,860,874 B2 | 3/2005 | Gubernick et al. | |
| 6,887,226 B2 * | 5/2005 | Cassoni et al. | 604/385.18 |
| 7,112,192 B2 * | 9/2006 | Hasse et al. | 604/385.17 |
| 7,335,194 B2 * | 2/2008 | Wada | 604/385.17 |
| 7,378,566 B2 * | 5/2008 | Soerens et al. | 604/365 |
| 2001/0011169 A1 * | 8/2001 | Taylor et al. | 604/385.18 |
| 2001/0014348 A1 | 8/2001 | Schoelling | |
| 2002/0120246 A1 * | 8/2002 | Buzot | 604/385.17 |
| 2002/0156442 A1 * | 10/2002 | Jackson et al. | 604/378 |
| 2003/0153864 A1 * | 8/2003 | Chaffringeon | 604/15 |
| 2003/0167048 A1 * | 9/2003 | Policappelli | 604/385.17 |
| 2003/0191443 A1 * | 10/2003 | Taylor et al. | 604/385.18 |
| 2004/0030316 A1 | 2/2004 | Gubernick et al. | |
| 2004/0116885 A1 * | 6/2004 | Soerens et al. | 604/378 |
| 2005/0096620 A1 * | 5/2005 | Awolin et al. | 604/385.18 |
| 2005/0096621 A1 * | 5/2005 | Almond | 604/385.18 |
| 2005/0096622 A1 * | 5/2005 | Almond | 604/385.18 |
| 2005/0177090 A1 * | 8/2005 | Jensen | 604/14 |
| 2005/0251979 A1 | 11/2005 | Friese et al. | |
| 2005/0256482 A1 | 11/2005 | Minoguchi et al. | |
| 2006/0036228 A1 * | 2/2006 | Noda et al. | 604/385.17 |
| 2006/0074391 A1 * | 4/2006 | Hagberg et al. | 604/385.18 |
| 2006/0247592 A1 | 11/2006 | Schmidt-Forst et al. | |
| 2007/0005039 A1 * | 1/2007 | Biggs et al. | 604/385.18 |
| 2007/0016156 A1 | 1/2007 | Burgdorf et al. | |
| 2008/0154222 A1 * | 6/2008 | Chaffringeon | 604/361 |

* cited by examiner

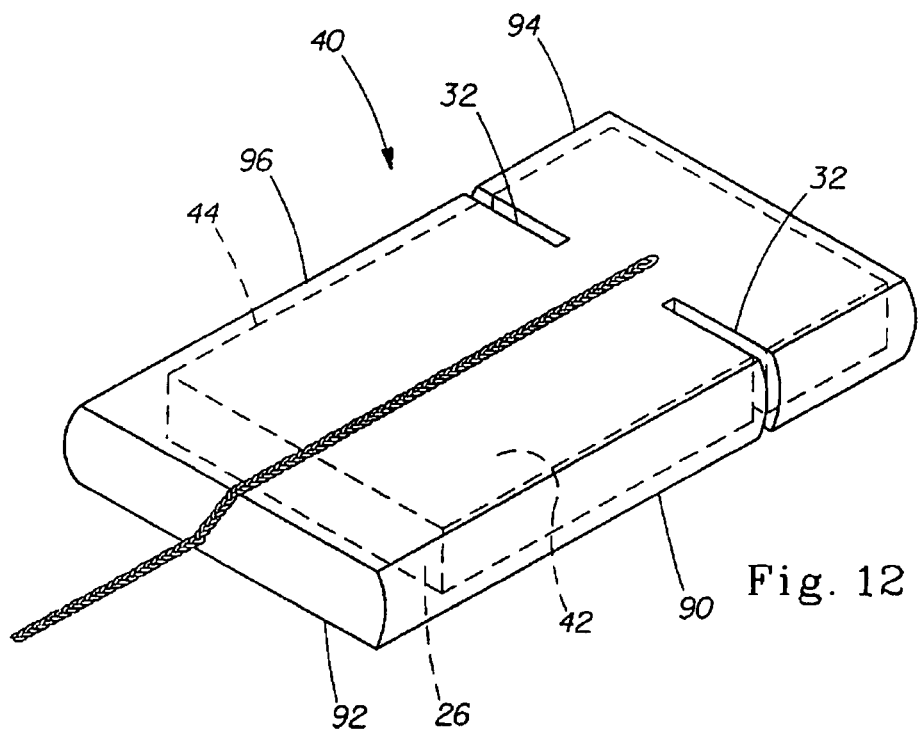
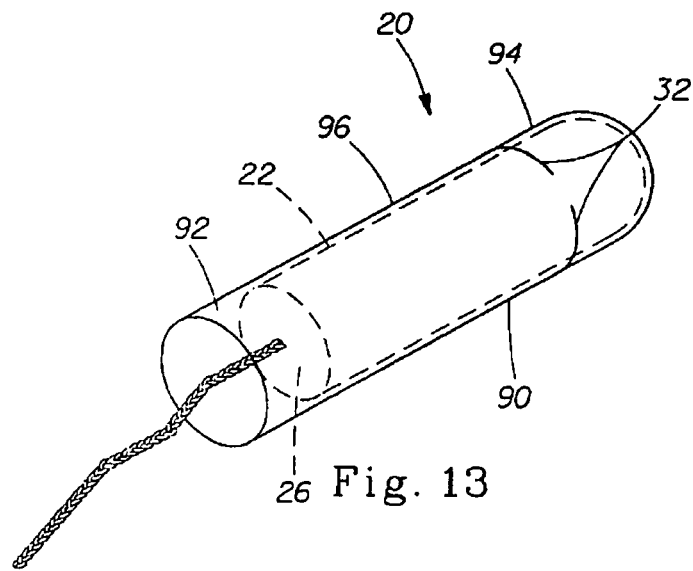

TAMPON HAVING AT LEAST ONE PHYSICAL DISCONTINUITY

FIELD OF THE INVENTION

The disclosed invention relates to tampons. More specifically, the disclosed invention relates to tampons having at least one physical discontinuity.

BACKGROUND OF THE INVENTION

During menstruation, leakage of menses from the vaginal opening is a frequent problem associated with the use of tampons. Leakage occurs when menses flows along the wall of the vaginal cavity, and out the vaginal opening without being absorbed by a tampon. One of the main reasons for the failure of a tampon to absorb menses is due to the physical limitations of the tampon. To be comfortably inserted into the vaginal cavity, the tampon should have a maximum diameter that is less than the diameter of the vaginal opening. To produce tampons with the desired vaginally insertable size, tampon pledgets are generally compressed into a rigid round cylindrical shape. Therefore, unless the tampon expands to contact and absorb the menses flowing along the walls of the vaginal cavity, the menses will exit the vaginal opening.

Tampons which are compressed rely upon the absorption of menses to generate expansion of the tampon. As there is little or no air in the vaginal cavity, expansion is limited to the volume of menses the tampon absorbs. However, expansion of the tampon is less than the volume of menses absorbed by the tampon, as some expansion potential is lost due to menses replacing air in the tampon. Therefore, the tampon expansion needed to provide protection against menses leakage is limited, especially at low levels of menses. Expansion of the tampon occurs in the direction opposite to which the tampon was compressed. For example, tampons that have been compressed in their length dimension expand primarily in a lengthwise direction. To provide the proper shape for insertion, tampons are primarily compressed radially and/or along their width and length dimensions. However, these compression strategies alone do not effectively maximize the expansion of the tampon.

Attempts in the prior art to control the expansion of tampons in the vaginal cavity have relied on tampons that are capable of dry expansion. Such tampons do not depend on the absorption of menses to cause expansion, and can expand within the vaginal cavity when there is little or no menses present in the vaginal cavity. These tampons are often formed from foam materials. The foam material is compressed in an applicator, and upon release from the applicator the material assumes its uncompressed shape within the vaginal cavity. The uncompressed shape of the tampon contacts the vaginal walls, as the diameter of the uncompressed tampon is greater than the diameter of the vaginal cavity. However, the dry expanding tampons also have several disadvantages. One disadvantage is that the dry expanding tampons can irritate the walls of the vaginal cavity, especially if there is little or no menses in the vaginal cavity. The irritation of the vaginal walls is caused by the tampon expanding and adhering to dry areas of the vaginal cavity that do not contain menses. Further, the tampons function as sponges in that they absorb the menses within the vaginal cavity, but when pulled through the vaginal opening they become constricted, which causes the release of the absorbed menses.

In addition, the prior art has tried to control the expansion of tampons to prevent the leakage of menses. Such control allows a portion or portions of the tampon to expand more or less than other portions of the tampon. For example, a tampon may be produced so that the center section of the tampon is capable of greater expansion than other portions of the tampon. These tampons typically restrict the expansion of certain portions according to a pre-determined pattern. For instance, an adhesive or bonding agent may be applied to, or incorporated into, a tampon to selectively prevent a portion of the tampon from expanding to the same degree that another portion expands when the tampon absorbs menses. The restriction in expansion of portions of the tampon has the disadvantage of reducing the amount of menses that the tampon may absorb, reducing the tampon's effectiveness.

What is needed in the art is a tampon that will substantially prevent the leakage of menses from the vaginal opening. Specifically, a tampon that can prevent leakage of menses when flow is at low levels, without causing discomfort to the user, and which overcomes the shortcomings of the tampons in the prior art.

SUMMARY OF THE INVENTION

A tampon is provided which comprises a compressed absorbent member. The compressed absorbent member has disposed therein at least one physical discontinuity.

A compressed tampon is provided which comprises a pledget. The pledget when uncompressed has a length, a width and two side edges, and wherein the pledget comprises at least one physical discontinuity. The physical discontinuity originates in one of the side edges and extends toward the other side edge and defines a first portion and a second portion.

BRIEF DESCRIPTION OF THE DRAWINGS

FIG. 12 is a perspective view of a pledget having an overwrap.

FIG. 13 is a perspective view of a tampon having an overwrap.

DETAILED DESCRIPTION OF THE INVENTION

Figure 1:
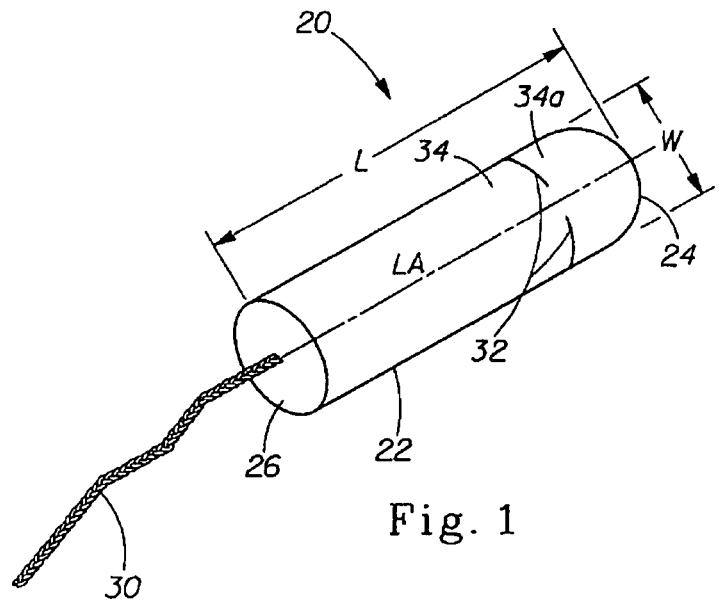
FIG. 1 is a perspective view of a tampon having at least one physical discontinuity.

FIG. 1 shows one embodiment of a tampon 20 of the present invention. The present invention, however, is not limited to a structure having the particular configuration shown in the drawings. The terms listed below will be used throughout the specification to describe the present invention.

The term "attached", as used herein, encompasses configurations in which a first element is directly secured to a second element. Attached also includes configurations in which the first element is indirectly secured to the second element by securing the first element to at least one intermediate member, which in turn is secured to the second element. Additionally, the term attached covers configurations in which the first element is integral with the second element, such that the first element is part of the second element.

As used herein, the term "tampon pledget", or "pledget", refers to a construction of absorbent material prior to compression of such construction into the absorbent member of a tampon. Tampon pledgets are sometimes referred to as a tampon blank, or a softwind.

As used herein, the term "cross-section", or "cross-sectional", refers to the plane which extends laterally through the tampon, and which is orthogonal to the longitudinal axis of the tampon.

As used herein, a first material is "substantially covering", or "substantially covers", a second material when the first material covers from at least about 50% to about 100% of the surface area of the second material. Further, a first material substantially covers a second material, when the first material covers a third material, which covers the second material. As such, a first material may "substantially cover" a second material regardless of whether a third material, or even a fourth material, is interposed between the first material and the second material.

An embodiment of a tampon 20 of the present invention is illustrated in FIG. 1. The tampon 20 is designed to be inserted into a woman's vaginal cavity to prevent menses from exiting the vaginal opening by contacting and absorbing the flow of menses. The term "menses", as used herein, is understood by one of ordinary skill in the art to include blood, tissue debris, and other bodily fluids emitted from the vaginal opening. The tampon 20 comprises a compressed generally cylindrical shaped absorbent member 22, (absorbent member), two physical discontinuities 32, and a withdrawal means 30. In certain embodiments, the generally cylindrical shape of the absorbent member 22 has a cross-section that is at least one of an oval, circle, square, rectangle, or any other cross-sectional shape known in the art. The tampon 20 has an insertion end 24 and a withdrawal end 26. The tampon 20 also has a longitudinal axis "LA" and a length "L". The length "L" of the tampon 20 is the measurement of the tampon 20 along the longitudinal axis originating at one end (withdrawal 26 or insertion 24) of the tampon 20, and ending at the opposite end (withdrawal 26 or insertion 24) of the tampon 20. A tampon may be straight or non-linear in shape, such as curved along the longitudinal axis. In certain embodiments, the tampon is 30-60 mm in length. Further, the tampon 20 has a width "W", which unless otherwise stated in the specification, corresponds to the greatest cylindrical cross-section along the length of the tampon 20. In certain embodiments, the tampon is 8-20 mm wide.

Figure 2:
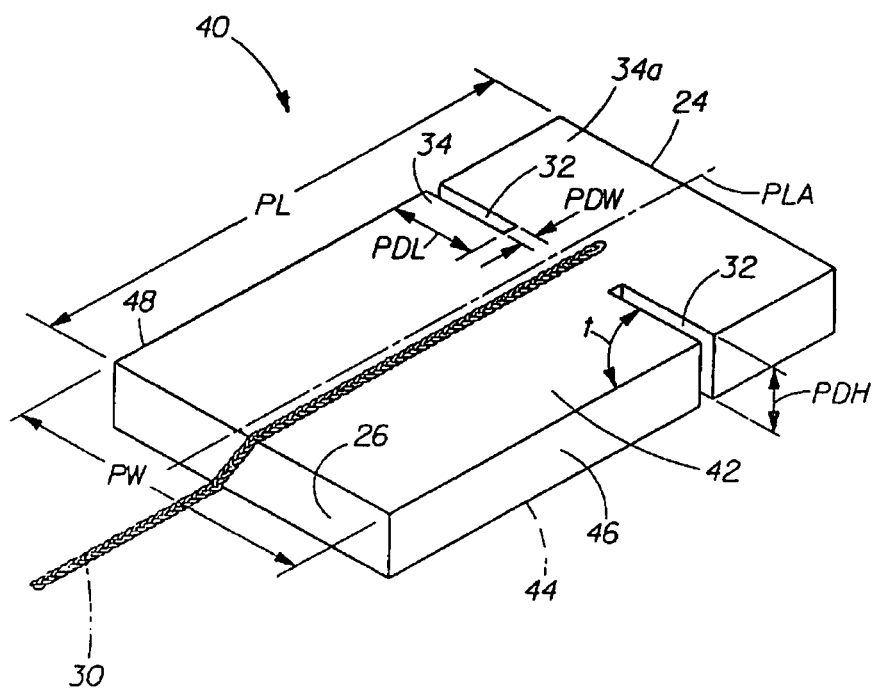
FIG. 2 is a perspective view of a pledget having two physical discontinuities.
Figure 3:
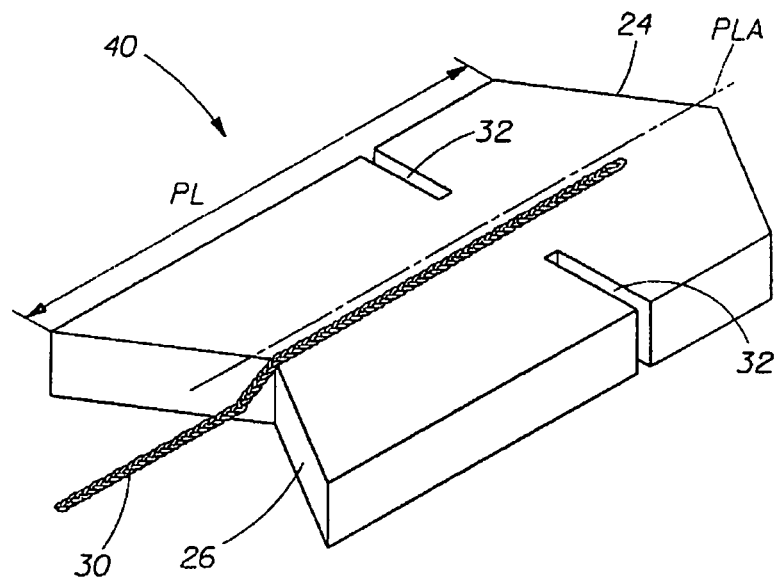
FIG. 3 is a perspective view of a chevron shaped pledget having at least one physical discontinuity.

As shown in FIGS. 2-9, the absorbent member of a tampon may be formed from a pledget 40. The pledget 40 of FIG. 2 has a withdrawal means 30, two physical discontinuities 32, a first surface 42, second surface 44, first side edge 46, second side edge 48, insertion end 24, and a withdrawal end 26. Pledgets 40 may have a square or rectangular shape, but other shapes may be used such as trapezoidal, triangular, or semi-circular. As shown in FIG. 3 in certain embodiments, a chevron shape can also be used. Referring back to FIG. 2, the pledget 40 has a longitudinal axis "PLA" and a length "PL".

The length of the pledget 40 is the measurement of the maximum distance along the longitudinal axis between one end (withdrawal 26 or insertion 24) of the pledget 40 and the opposite end (withdrawal 26 or insertion 24) of the pledget 40. For example, as shown in FIG. 3 if the pledget 40 has a shape other than square or rectangular, such as a chevron, the length of the pledget 40 would be a measurement of the maximum distance between the withdrawal end 26 and the insertion end 24, as measured along the longitudinal axis. As shown in FIG. 2, the pledget 40 also has a width "PW". The width is a measurement of the maximum distance between the first side edge 46 and second side edge 48 of the pledget 40.

A pledget is compressed to form the absorbent member of a tampon, such as the absorbent member 22 of FIG. 1. The absorbent member can have a folded construction as described in co-pending application U.S. application Ser. No. 10/887,645, wherein the pledget has a multiplicity of parallel folds along the longitudinal axis, which can be provided prior to, and/or as a result of a compression step. In certain other embodiments, the pledget prior to compression may be rolled, comprise a "petal" structure, or any of the other structures a tampon pledget may assume prior to, and during compression, which are known to those of ordinary skill in the art.

The pledget 40 may be of a size and thickness that can be compressed into an absorbent member of a tampon having a vaginally insertable shape. The pledget 40 may be a laminar structure comprising individual distinct layers of absorbent material. In those embodiments wherein the tampon pledget 40 comprises a laminar structure, the discrete layers may be formed from a single absorbent material and/or from differing absorbent materials. In certain embodiments, the size of the pledget 40 may be from about 40 mm to about 100 mm in length, and from about 40 mm to about 80 mm in width. In certain embodiments, the range for the overall basis weight of the pledget 40 is from about 150 gsm (g/m2) to about 1,500 gsm.

Figure 4:
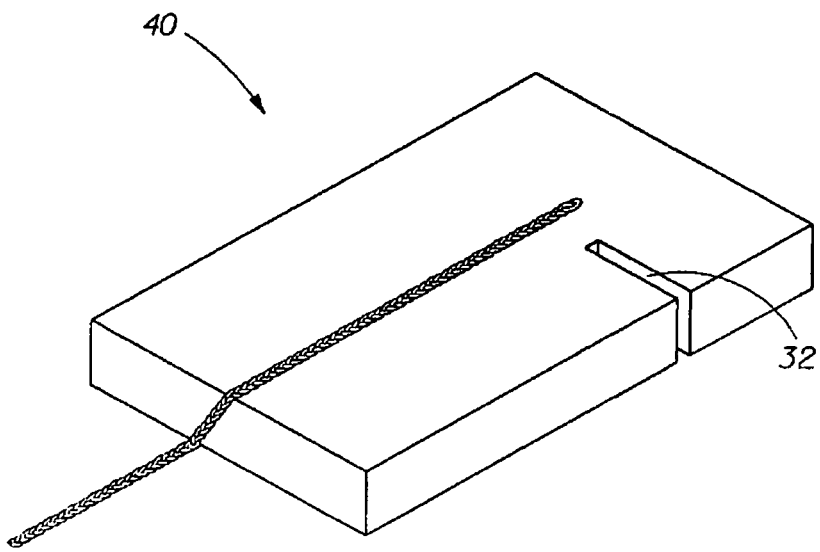
FIG. 4 is a perspective view of a pledget having one physical discontinuity.
Figure 5:
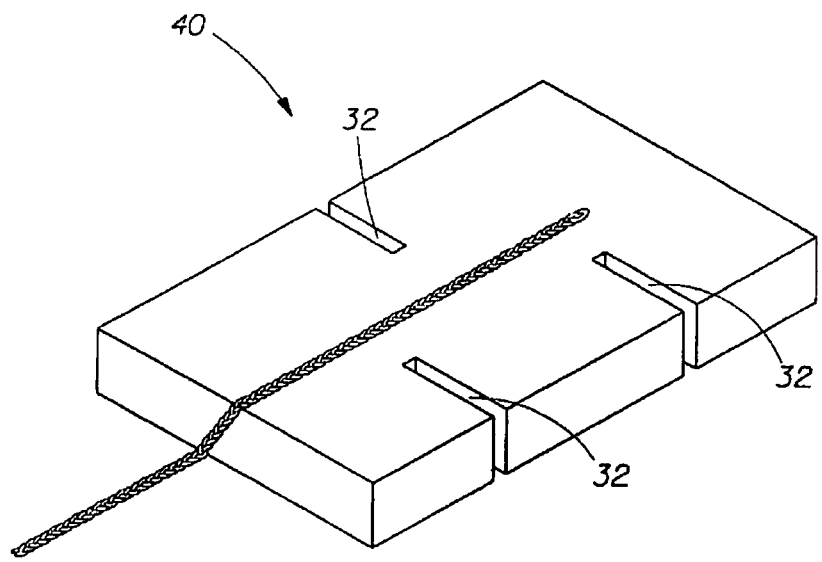
FIG. 5 is a perspective view of a pledget having three physical discontinuities.

As shown in FIG. 2, the pledget 40 has at least one physical discontinuity 32, wherein the physical discontinuity 32 may be in the form of a slit, slot or notch, which physically severs the absorbent material. For example, the physical discontinuities 32 shown in FIG. 2 are notches. A physical discontinuity 32 divides the pledget 40, into opposing portions, a first portion 34 and a second portion 34A along the length "PDL" of the physical discontinuity 32. It should be noted that while FIG. 2 shows two physical discontinuities 32, the present invention is not limited to the embodiment shown in FIG. 2, in that the present invention encompasses pledgets 40 comprising a single physical discontinuity 32, as shown in FIG. 4, and those embodiments having more than two physical discontinuities 32, as shown in FIG. 5. In certain embodiments, the physical discontinuity 32 originates on one side edge (first side edge 46 or second side edge 48) of the pledget 40, and extends inwardly to the opposing side edge (first side edge 46 or second side edge 48) of the pledget 40. The physical discontinuity 32 may have any length along the width of the pledget 40. In certain embodiments, a physical discontinuity 32 may have a length that is between about one-third (⅓) to about two-thirds (⅔) the width of the pledget 40. A physical discontinuity 32 may be linear or non-linear such as a curve, along a part or the whole length of the physical discontinuity 32.

Figure 6:
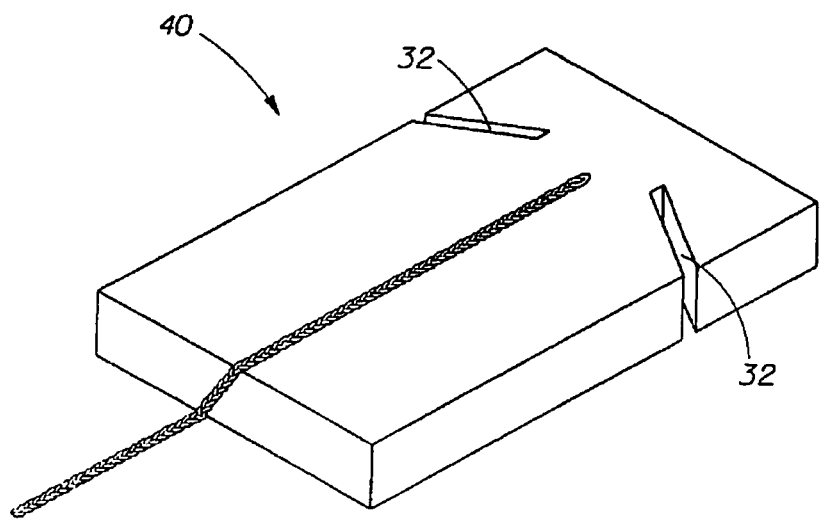
FIG. 6 is a perspective view of a pledget wherein the physical discontinuities are angled.

A physical discontinuity 32 has a width "PDW", which is the distance between opposing portions 34, 34A of the pledget 40 along the length of the physical discontinuity 32. In certain embodiments, a physical discontinuity 32 has a width that is from 0 to about 20 mm. In certain embodiments, the width of a physical discontinuity 32 may vary along the length of the physical discontinuity 32. A physical discontinuity 32 has a height "PDH" as measured between the first surface 42 and second surface of the pledget 40. A physical discontinuity 32 has an angle "t" as measured from the first 46 or second side edge 48 of the pledget 40 that is from greater than zero (0) degrees to less than about one-hundred and eighty (180) degrees. In certain embodiments, the physical discontinuity 32 has an angle of about ninety (90) degrees. As physical discontinuities 32 may be of an angle from zero (0) degrees to less than about one-hundred and eighty (180) degrees, physical discontinuities 32 in certain embodiments may be angled (have an angle other than ninety (90) degrees) on the pledget 40 as shown in FIG. 6. A physical discontinuity 32 may be present anywhere along the length of the pledget 40. For example, at least one physical discontinuity may be present about 10 mm to about 20 mm from the insertion end 24 of the pledget 40. After the pledget 40 is compressed the physical discontinuities 32 of the pledget 40 form the physical discontinuities 32 of the tampon 20 as shown in FIG. 1.

Figure 7:
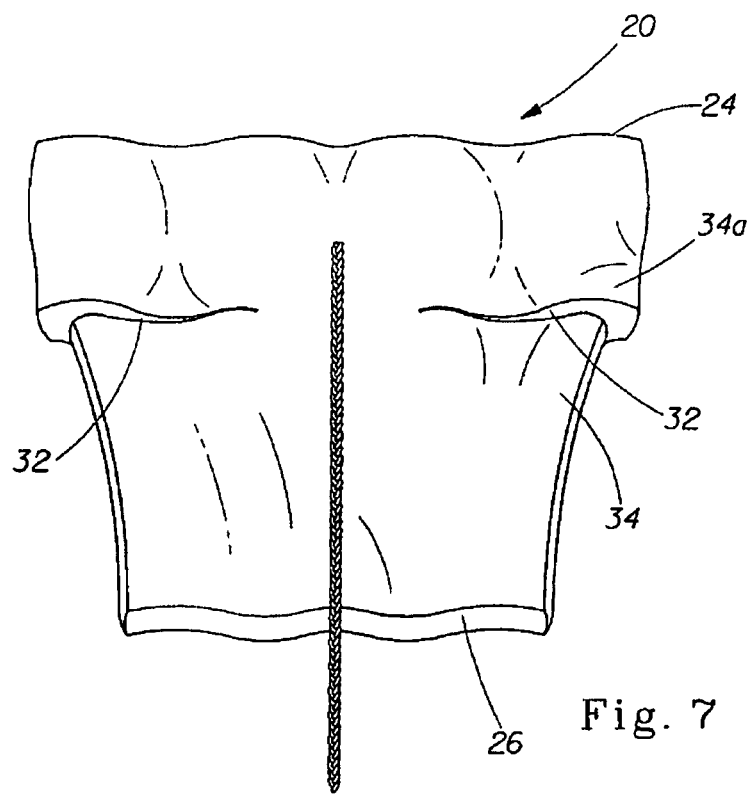
FIG. 7 is a perspective view of a partially expanded tampon.

The physical discontinuities in the pledget and tampon serve to control the expansion of a tampon upon absorption of menses. In certain embodiments, the physical discontinuities in the pledget and tampon are positioned in such a manner to partially isolate the portion of the tampon that will first absorb menses first, from the other portions of the tampon. As used herein, the terms "partially isolated", or "to partially isolate", refer to the state of a portion of a tampon which will absorb menses, wherein the portion does not have substantial fluid contact with a portion of the tampon on the opposite side of a physical discontinuity. As a portion or portions of a tampon, which first absorb the menses, are partially isolated from the other portion or portions of the tampon the partially isolated portion or portions may expand independently from the other portions of the tampon. While not being limited to theory, it is believed that the presence of a physical discontinuity retards or prevents fluid transfer between the portions of the tampon separated by a physical discontinuity. This partial isolation of a portion or portions concentrates menses absorption and, therefore, increases the level of expansion in the portion of the tampon, which initially absorbs the menses. Wherein as used herein the term "level of expansion", refers to the width of a portion of the tampon, after the tampon has absorbed menses. In certain embodiments, portions of a tampon, which are partially isolated from other portions of the tampon, may have a higher level of expansion than the other portions. For example, in certain embodiments, the saturated portion's width is at least 10% greater than other portions of the tampon. For example, as shown in FIG. 7, if the menses was first absorbed by a tampon 20 in a portion of the tampon 20 closest to the insertion end 24 which was partially isolated from rest of the tampon 20 by a physical discontinuity 32, the partially isolated second portion 34A would have a higher level of expansion than the opposing first portion 34 of the tampon 20.

The portion or portions of the tampon, which are partially isolated from the other portions of the tampon, may be positioned on the tampon where menses is first expected to be absorbed. For example, menses enters the vaginal cavity through the cervix. Therefore, upon insertion, the insertion end of the tampon would contact and absorb the menses before other portions of the tampon. As such, the portion of a tampon near the insertion end may be partially isolated from the other portions of the tampon. This allows the portion of the tampon near to the insertion end to quickly expand close the source of the menses, and prevent the menses from flowing along the walls of the vaginal cavity without being absorbed by the tampon.

Alternately, a portion or portions of the tampon at or near the withdrawal end of the tampon may be partially isolated from the other portions of the tampon. For example, the vaginal cavity is narrower near the vaginal opening than it is near the cervix. Therefore, upon insertion, the withdrawal end can contact a larger portion of the vaginal wall, compared to the insertion end, and would more likely absorb fluid before it exits the vaginal cavity.

The cross-section of a tampon may also affect where the physical discontinuities are positioned. For example, the cervix extends into the vaginal cavity, and a tampon having an oval or slightly flattened cross-section, allows the insertion end of the tampon to be positioned above or below the cervix. This allows the insertion end of the tampon to first contact the menses. Therefore, a physical discontinuity may be positioned at or near the insertion end of the tampon such that the absorption of menses, and the consequent expansion of the insertion end are not substantially influenced by other portions of the tampon on the opposing side of the physical discontinuity.

Figure 8:
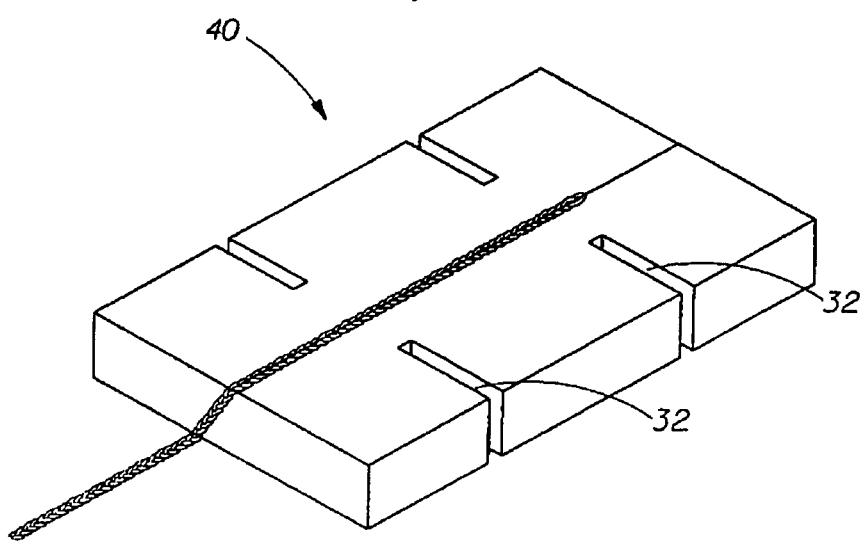
FIG. 8 is a perspective view of a pledget having multiple pairs of physical discontinuities.

Referring back to FIG. 2, physical discontinuities 32 may be arranged in at least one pair along the length of the pledget 40. In each pair there will be a physical discontinuity 32 originating on each side edge 46 or 48 of the pledget 40 at about the same position along the length of the pledget 40, with each physical discontinuity 32 extending towards the opposing physical discontinuity 32 along the width of the pledget 40. In certain embodiments, as shown in FIG. 8, a pledget 40 may have more than one pair of physical discontinuities 32. Multiple physical discontinuities would partially isolate multiple portions of the tampon, allowing for more than one portion of a tampon to have a different level of expansion as compared to other portions. FIG. 2 shows that the height of a physical discontinuity 32 may completely traverse a pledget 40, such that the physical discontinuity 32 is open to the first 42 and second surfaces 44 of the pledget 40. In certain other embodiments, the height of a physical discontinuity may be such that the physical discontinuity does not completely traverse the pledget. For example, the physical discontinuity may only be open to one surface of the pledget, or the pledget may be open to neither surface. The physical discontinuities 32 in the pledget 40 or tampon 20 can be made by cutting or removing the absorbent material using any method known in the art such as die cutting, water jet, rotary knife, and laser.

In addition to being divided by physical discontinuities, portions of a tampon may differ in composition. For example, the basis weight of absorbent material may be higher in the portion, which has a different level of expansion as compared to the portion on the opposing side of a physical discontinuity. Different levels of expansion could also be attained by varying the composition of the absorbent material between the portions, such as by the addition of highly resilient synthetic fibers to one portion and not the opposing portion.

In certain embodiments, to differ the level of expansion of portions of a tampon, the tampon would have portions of differing dry density (density). The stability and level of expansion of a portion may be increased by increasing the portion's density in relation to other portions. For example referring to FIG. 1, if increased expansion is desired in the insertion end 24 of the tampon 20, the second portion 34A of the tampon 20 above the physical discontinuities 32 would have a higher density, (about 0.5 g/cc (grams per cubic centimeter) to about 0.7 g/cc) in comparison to the density of the first portion 34 of the tampon 20 below the physical discontinuities 32 (0.3 g/cc to about 0.4 g/cc). The densities of different portions within the tampon can be produced by providing a pledget having varying thickness, with the portions of the pledget having the greater thickness corresponding to those portions of the tampon having a greater density. Additionally, greater densities can be produced in a compressed tampon by having a pledget with multiple layers in the portions, which correspond to the portions of the compressed tampon having higher densities. Therefore, a pledget formed from a single layer may have additional layers applied to the portions, which will form the portions of the compressed tampon having higher densities.

Figure 9:
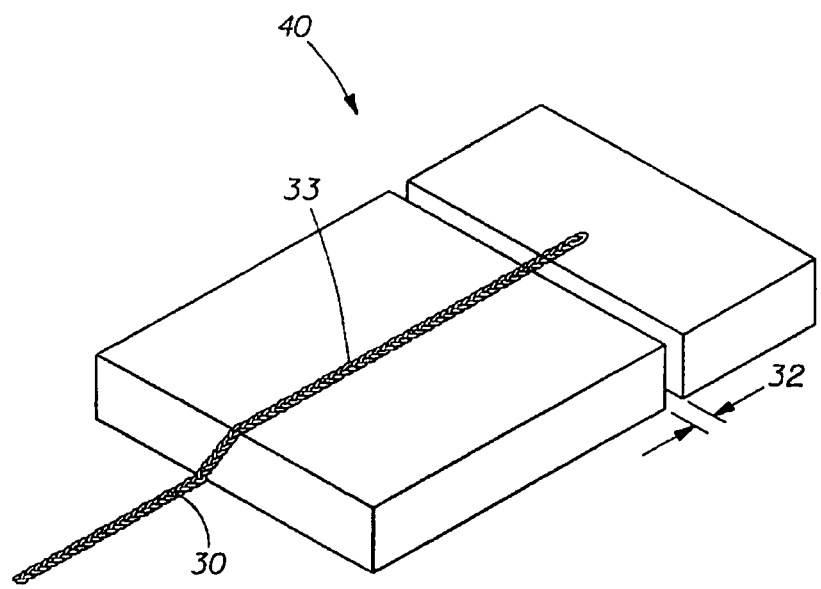
FIG. 9 is a perspective view of a pledget having a single physical discontinuity.

In certain embodiments, as shown in FIG. 9, one or more physical discontinuities 32 as described above may have a length, which completely bisects the width of a pledget 40. The portions that are formed may be attached to each other through a secondary absorbent member 33 and/or withdrawal means 30. The secondary absorbent member 33 and withdrawal means 30 are described below.

Figure 10:
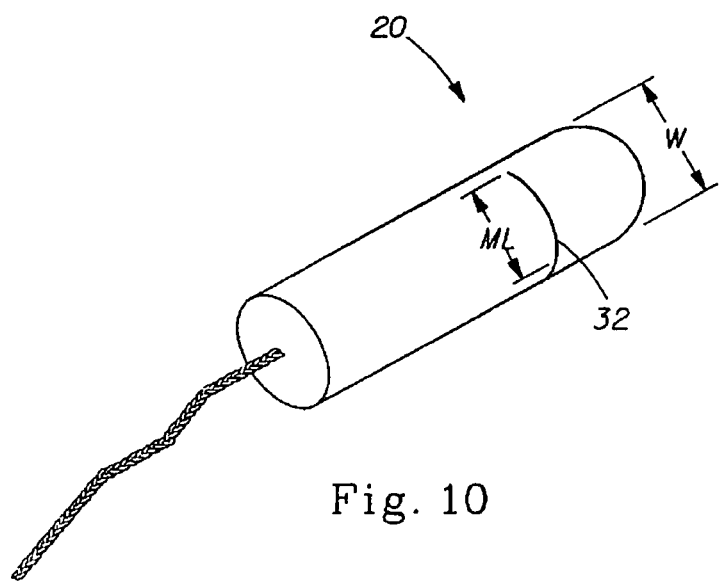
FIG. 10 is a perspective view of a tampon having a physical discontinuity, wherein the physical discontinuity was made after the tampon had been compressed.

As shown in FIG. 10, in certain embodiments, at least one physical discontinuity 32 may be made to a previously compressed tampon 20. The height of the physical discontinuity 32 can be such that the physical discontinuity 32 does not completely sever the tampon 20 into two or more parts not connected by absorbent material, secondary absorbent member, or withdrawal means. The length "ML" of the physical discontinuity 32 extends across the width "W" of the tampon 20. The physical discontinuity 32 can be located anywhere along the length of the tampon 20.

Figure 11:
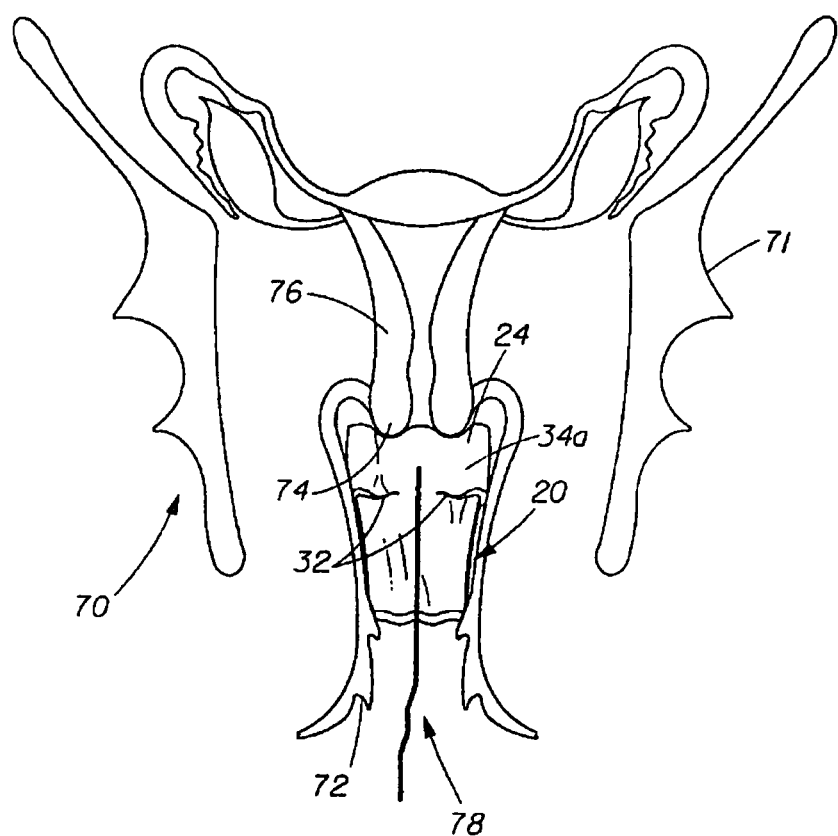
FIG. 11 is a frontal section of the lower part of a human torso showing a tampon positioned in the vaginal canal.

In certain embodiments, as shown in FIG. 11 the portion of the tampon 20 that first absorbs the menses will be the second portion 34A of the tampon 20 near the insertion end 24. FIG. 11 depicts a frontal cross-sectional view of the lower torso 70 of a human female, which includes a vaginal cavity 72, a cervix 74, and a uterus 76, all of which are bordered by the pelvic girdle 71. The vaginal cavity 72 has an introital or vaginal opening 78 which exits the lower torso 70. As shown in FIG. 11, the second portion 34A of the tampon 20 which initially absorbs the menses is near the insertion end 24 of the tampon 20 which is positioned in close proximity to the cervix 74. After absorbing menses, the second portion 34A expands to prevent the leakage of menses from the vaginal opening 78.

The pledget and, consequently, the compressed absorbent member of the tampon may be constructed from absorbent materials such as fibrous materials. Such fibrous materials may include, but are not limited to synthetic fibers, natural fibers, or combinations thereof. The natural fibers may include, but are not limited to, cotton, wood pulp, flax, hemp, and rayon, such as GALAXY Rayon (a tri-lobed rayon structure) available as 6140 Rayon; or SARILLE L rayon (a round fiber rayon), both available from Kelheim Fibers of Kelheim, Germany, cotton, wood pulp, flax, and hemp. The synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. Additional absorbent material include materials such as, peat moss, absorbent foams (such as those disclosed in U.S. Pat. No. 3,994,298), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), may be incorporated into the tampon.

As shown in FIG. 12, a tampon pledget 40 may be substantially covered by an overwrap 90, such as those described in U.S. Pat. No. 6,840,927. As used herein, "overwrap" refers to materials that substantially cover the first surface 42 and second surface 44 of the pledget 40. In certain embodiments, the overwrap 90 substantially covers the pledget 40 before physical discontinuities 32 are made in the pledget 40, such that the physical discontinuities 32 are also made in the overwrap 90. In certain other embodiments, the overwrap 90 substantially covers the pledget 40 after the physical discontinuities 32 are made in the pledget 40, such that there are no physical discontinuities in the overwrap 90. In certain embodiments, the overwrap 90 extends beyond the withdrawal end 26 of the pledget to form a skirt 92. The overwrap 90 may be formed from nonwoven fibrous materials or apertured films. The nonwoven fibrous materials may comprise fibrous materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate or bicomponent fibers, such as bicomponent polyethylene and polypropylene fibers. In one embodiment, the overwrap 90 comprises bicomponent polyethylene and polypropylene fibers wherein the fibers have a basis weigh of about 18 gsm (grams per square meter). The blend of fibers forming the overwrap 90 can be made by any number of techniques, such as being spunbond or carded. Commonly, carded webs that are hydroentangled, thermally bonded, and resin bonded, all may be used with the pledget and tampon of the present invention.

As shown in FIG. 13, the overwrap 90 may substantially cover the exterior surface of the compressed absorbent member 22 of the tampon 20, as well as any interior surfaces or interior regions that result from the folding or rolling of the absorbent material during compression. The overwrap 90 transports menses over the surface of a tampon prior to absorption of the menses into the compressed absorbent member 22. In certain embodiments, the overwrap 90 extends beyond the withdrawal end 26 of the absorbent member 22 to form a skirt 92. The overwrap 90 may have non-uniform properties. As shown in FIGS. 11 and 13, the overwrap 90 may have regions 94 and 96 with differing properties that correspond to the portions formed by the physical discontinuities 32. The regions 94 and 96 of the overwrap 90 may be coordinated with the portions of the tampon 20 to increase or decrease absorbency, and/or level of expansion of the tampon portions. For example, a certain region 94 and 96 of the overwrap 90 may be more hydrophilic or hydrophobic in comparison to other regions 94 and 96 of the overwrap 90. In certain embodiments, the hydrophilic region 94 and 96 of the overwrap 90 could substantially cover the portion of the tampon 20 that would contact the menses first to increase menses absorption and as a result increase expansion of that portion of the tampon 20.

The regions 94 and 96 of the overwrap 90 with differing properties may be produced by various means. One such means is by treating regions 94 and 96 of the overwrap 90 with chemical finishes, such as hydrophilic or hydrophobic finishes that make the regions 94 and 96 treated there with either more hydrophilic or hydrophobic, respectively. The regions 94 and 96 of the overwrap 90 may also be mechanically altered. Any means known in the art of mechanically altering non-wovens or films can be used to produce overwraps for the present invention. Mechanically altering includes such processes as ring rolling or "corrugating", SELFing, and aperturing. One method of SELFing is disclosed in U.S. Pat. No. 5,518,801. Known methods of aperturing include hot pin as disclosed in U.S. Pat. No. 5,188,625, physical discontinuity and stretch as disclosed in U.S. Pat. No. 5,714,107, and selectively aperturing as disclosed in U.S. Pat. No. 5,916,661.

The overwrap's 90 composition may also provide differing properties. Different regions 94 and 96 of the overwrap 90 may be produced from different materials. For example, one region 94 and 96 of the overwrap 90 may have a higher concentration of rayon than the other sections of the overwrap 90 to make that region more hydrophilic. Materials could be selected for any property desired for overwraps known in the art, such as a selection of a material to provide a region 94 and 96 of the overwrap 90 with greater extensibility. Further, the overwrap 90 may comprise multiple discrete pieces that are attached to form a single overwrap 90. The discrete pieces may have differing properties which may be produced as described above. Further, in certain embodiments, the discrete pieces of the overwrap 90 may form the regions 94 and 96 of the overwrap 90. For example, one discrete piece may form one region 94 and 96 of the overwrap 90 and another discrete piece may form the other region 94 and 96 of the overwrap. The discrete pieces may be attached by any method known to one of ordinary skill in the art, such as sewing, adhesive, thermal bonding, fusion bonding, or combinations thereof.

In certain embodiments, the overwrap substantially covers the compressed absorbent member subsequent to compression of the tampon pledget. The overwrap may be wrapped around the longitudinal axis, or transverse axis, of the compressed absorbent member. The overwrap is positioned on the compressed absorbent member such that the overwrap substantially covers the exterior surface of the compressed absorbent member. Overwraps attached subsequent to compression should be extensible such that the tampon will be able to expand within the vaginal cavity. The overwrap may be attached to itself, another overwrap, the compressed absorbent member, or tampon pledget. Such attachment may extend continuously along the length of attachment, or it may be applied in a "dotted" fashion at discrete intervals.

The pledget and tampon may also comprise a secondary absorbent member to which a withdrawal means may be connected. The withdrawal means may be integral with the secondary member, or it may be a separate component, which is either attached to the secondary member or attached directly to the absorbent member. The withdrawal means may be attached to the secondary absorbent member, or absorbent member, by any manner known in the art, such as sewing, adhesive, thermal bonding, fusion bonding, or combinations thereof. U.S. Pat. No. 6,258,075 describes tampons having a variety of secondary absorbent members in detail. The secondary absorbent member serves as a further means to prevent the leakage of menses from the vaginal cavity. The secondary absorbent member may be attached to the withdrawal means, the compressed absorbent member or both.

The pledget, and consequently the tampon of the present invention, may comprise a withdrawal means such as a string, cord, or any other means as known in the art. The withdrawal means may be joined to any suitable location on the tampon and graspable for digital removal after use. In certain embodiments, the withdrawal means is attached to the compressed absorbent member and pledget, and extends beyond the withdrawal end of the compressed absorbent member. In addition to a string or cord configuration, the withdrawal means may have other configurations such as a ribbon, loop, or tab. Withdrawal cords that may be used in the present invention can be made of any material known in the art, such as cotton, or polyester. The withdrawal means may be integral with, or an extension of, another element of the tampon, such as an overwrap as described above.

The tampon of the present invention may be inserted digitally, or with the use of an applicator. Any of the currently available tampon applicators may also be used for insertion of the tampon of the present invention. Such applicators are typically of a "tube and plunger" type arrangement and may be plastic, paper, or other material known in the art. Additionally, a "compact" type applicator may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compressed tampon comprising:
    a pledget comprising a first absorbent material, a second absorbent material, and at least one physical discontinuity in the form of a slit, slot, or notch, wherein the at least one physical discontinuity originates on a side edge of the pledget and extends towards an opposing side edge of the pledget to define a partially isolated first portion and second portion, and wherein the slit, slot, or notch physically severs at least one of the first absorbent material and the second absorbent material, and wherein the first absorbent material is different from the second absorbent material;
    a withdrawal end and an insertion end; and
    a longitudinal axis.

2. The tampon of claim 1, wherein the physical discontinuity permits the first portion and the second portion to have different levels of expansion.

3. The tampon of claim 2 wherein the first portion has a higher level of expansion than the second portion.

4. The tampon of claim 2, wherein the second portion has a higher level of expansion than the first portion.

5. The tampon of claim 1, wherein the first portion is nearer a withdrawal end and the second portion is nearer an insertion end.

6. The tampon of claim 1, wherein the first absorbent material and the second absorbent material are at least one of synthetic fibers, natural fibers, or combinations thereof.

7. The tampon of claim 1, wherein the first absorbent material of the first portion and the second absorbent material of the second portion have different basis weights.

8. The tampon of claim 1 wherein the first portion and second portion have different dry densities.

9. The tampon of claim 1 wherein the tampon comprises an overwrap.

10. A compressed tampon comprising:
a longitudinal axis;
a withdrawal end and an insertion end; and
a pledget comprising an absorbent material and at least one physical discontinuity in the form of a slit, slot, or notch, wherein the at least one physical discontinuity originates on a side edge of the pledget and extends towards an opposing side edge of the pledget in a direction at an angle of about 90 degrees to the longitudinal axis to define a partially isolated first portion and second portion, and wherein the at least one physical discontinuity is located about 10 mm to about 20 mm from the insertion end, and wherein the physical discontinuity permits the first portion and the second portion to have different levels of expansion, and wherein the slit, slot, or notch physically severs the absorbent material.

11. A compressed tampon comprising:
a longitudinal axis;
a withdrawal end and an insertion end; and
a pledget comprising an absorbent material and at least one physical discontinuity in the form of a slit, slot, or notch, wherein the at least one physical discontinuity originates on a side edge of the pledget and extends towards an opposing side edge of the pledget to define a partially isolated first portion and second portion, and wherein the first portion is nearer the withdrawal end and the second portion is nearer the insertion end, and wherein the second portion has a higher level of expansion than the first portion, and wherein the slit, slot, or notch physically severs the absorbent material, and wherein the physical discontinuity has a width from about 1 mm to about 20 mm.

* * * * *